United States Patent [19]

Hammann et al.

[11] Patent Number: 4,812,408
[45] Date of Patent: Mar. 14, 1989

[54] BLOOD CULTURE SYSTEM

[75] Inventors: Rainer Hammann, Weisenbach; Friedrich Weber, Heildelberg; Peter Röhm, Plankstad, all of Fed. Rep. of Germany

[73] Assignee: Becton, Dickinson and Company, Franklin Lakes, N.J.

[21] Appl. No.: 235,765

[22] Filed: Aug. 24, 1988

Related U.S. Application Data

[63] Continuation of Ser. No. 171,215, Mar. 17, 1988, abandoned, which is a continuation of Ser. No. 56,518, Jun. 1, 1987, abandoned.

[51] Int. Cl.⁴ .................................. C12M 1/24
[52] U.S. Cl. .................. 435/296; 435/299; 215/276
[58] Field of Search ............ 435/299, 300, 296, 287; 215/227, 277, 276

[56] References Cited

U.S. PATENT DOCUMENTS

| | | | |
|---|---|---|---|
| 2,275,567 | 3/1942 | Smith | 435/300 |
| 2,793,776 | 5/1957 | Lipari | 215/6 |
| 2,813,649 | 11/1957 | Lipari | 215/11 |
| 3,083,145 | 3/1963 | Ryan | 435/300 |
| 3,589,983 | 6/1971 | Holderith et al. | 435/299 |
| 3,834,992 | 9/1974 | Bohnke et al. | 435/299 |
| 3,849,256 | 1/1974 | Linder | 435/300 |
| 4,023,693 | 2/1978 | Janin | 435/300 |
| 4,246,352 | 1/1981 | Buddmeyer | 435/299 |
| 4,308,347 | 12/1981 | Forrer | 435/299 |
| 4,355,111 | 10/1982 | Shimizu et al. | 435/299 |
| 4,640,895 | 2/1987 | Davis | 435/300 |
| 4,678,753 | 7/1987 | Hempel et al. | 435/296 |

FOREIGN PATENT DOCUMENTS

| | | | |
|---|---|---|---|
| 0111783 | 6/1984 | European Pat. Off. | 435/300 |
| 19589 | of 1892 | United Kingdom . | |

*Primary Examiner*—James C. Yeung
*Attorney, Agent, or Firm*—Mary M. Allen

[57] ABSTRACT

A culture bottle assembly for the detection of microorganisms in a fluid sample is provided. The culture bottle assembly is a container having an internal flange which divides the culture bottle into two compartments. A frame having a lower peripheral edge which mates with the internal flange is provided in one compartment. A cap is provided for the container and means are provided for moving the cap axially with respect to the container. A resilient material is provided on the peripheral edge of the cup which is compressed by the cap moving means to provide a liquid tight seal between the two compartments.

8 Claims, 2 Drawing Sheets

BLOOD CULTURE SYSTEM

This application is a continuation of application Ser. No. 171,215, filed Mar. 17, 1988, abandoned, which is a continuation of application Ser. No. 056,518, filed June 1, 1987, abandoned.

BACKGROUND OF THE INVENTION

1. Field of the Invention

The present invention relates to the detection of microorganisms in a fluid sample such as, for example, body fluids. More particularly, the present invention relates to a culture bottle assembly wherein a liquid nutrient medium is provided in combination with a solid medium and wherein a fluid sample is incubated in the liquid nutrient medium which is then used to inoculate the solid medium and to continue the growth of organisms which are initially grown in the liquid nutrient medium.

2. Prior Art

The detection of microorganisms in body fluids, particularly bacteria in blood, requires that a sample of the fluid be used to inoculate a liquid nutrient medium. Subsequently, the liquid medium is in turn used to inoculate a solid medium to continue the growth of the organisms and to make them visible to the naked eye as colonies.

Normal monophasic systems consist of a liquid medium in a culture bottle or vial which is inoculated with a sample of the fluid and is then incubated for a desired period of time (24-48 hours). After that, a sample is withdrawn from the bottle and is used to inoculate a solid nutrient medium (agar in a Petri dish).

This procedure is laborious, sometimes hazardous and includes the risk of contamination with microorganisms from the environment. Therefore detection systems have been developed in which liquid and solid culture media are combined in the same container. Such systems avoid the troublesome and sometimes hazardous transfer of the liquid culture to the solid culture medium. U.S. Pat. No. 2,992,974 to Belcove et al, for example, describes a biological testing device in which a solid medium is restrained in the top portion of a rectangular culture bottle while a liquid nutrient medium is provided in the lower most portion of the bottle. U.S. Pat. No. 3,589,983 to Holderith et al describes a culture bottle which is designed to hold a solid agar nutrient material at a location along the axial centerline of a bottle. The bottle also houses a liuid nutrient broth which may be separated from the solid agar by positioning the bottle on its side.

The above described prior art devices which combine a liquid nutrient medium in a single container with a solid medium have a major disadvantage in that the culture assembly must be positioned in a certain manner prior to contacting the solid medium with the precultured liquid medium. The above described prior art devices for separating solid and liquid culture media are complicated and facilitate separation of the liquid media and the solid media only during incubation, but not during transport.

U.S. Pat. No. 4,308,347 to Forrer et al describes a device for detection of microorganisms in a fluid sample which includes a first container holding a liquid nutrient medium and a second container containing one or more solid nutrient medium. The containers are detachably connected so that the media can be brought into contact when desired. The device described in the Forrer Patent is complicated and requires several manipulative steps to bring the precultured liquid media into contact with the solid medium.

The above disadvantages of the prior art are overcome in accordance with the present invention which provides a simple culture bottle assembly which contains a liquid media and one or more solid nutrient media in a single container with easily effected means for bringing the precultured liquid media into contact with the solid media when desired.

Summary of the Invention

In accordance with the present invention, a culture bottle assembly for the detection of microorganisms in body fluids is provided which is extremely simple and which avoids the disadvantages of the prior art. The culture bottle assembly of the present invention consists of a single container divided into a first lower compartment and a second upper compartment by an internal flange. A frame is provided for insertion into the second upper compartment. The frame has a lower peripheral edge which can be lowered into mating relationship with the internal flange. A resilient material is disposed on the lower peripheral edge. Closure means are provided which cause the frame to move downwardly and compress the resilient material against the flange to close the container and to provide two compartments which are sealed from each other. The first lower compartment contains a liquid nutrient medium and the second upper compartment contains one or more solid media. A fluid conduit is provided thru the frame whereby a specimen can be inserted through an aperture in the closure means into the fluid medium in the lower compartment. After a sample is incubated in the liquid medium for a desired period of time the closure means are moved to a second position which provides an open space above the internal flange through which the precultured liquid medium can be transferred into contact with the solid media when the container is turned over.

Further details and features of the invention will become more apparent from the following detailed description and the drawings which disclose what is presently considered to be the best mode of the invention.

THE DRAWINGS

In the drawings:

FIG. 1. is a longitudinal cross section of the container in accordance with the present invention which shows the relative location of the liquid nutrient medium and the solid medium;

DETAILED DESCRIPTION OF THE INENTION

Figure 1:
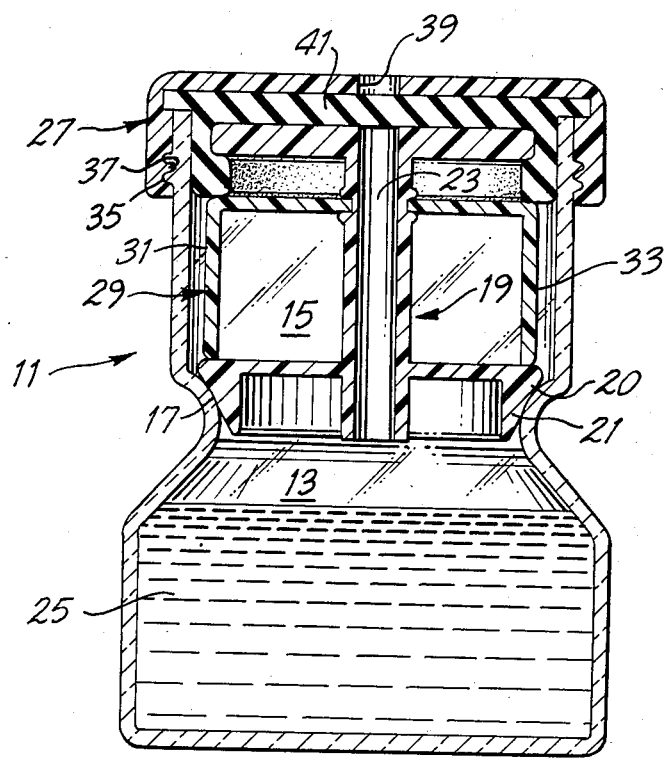
Figure 2:
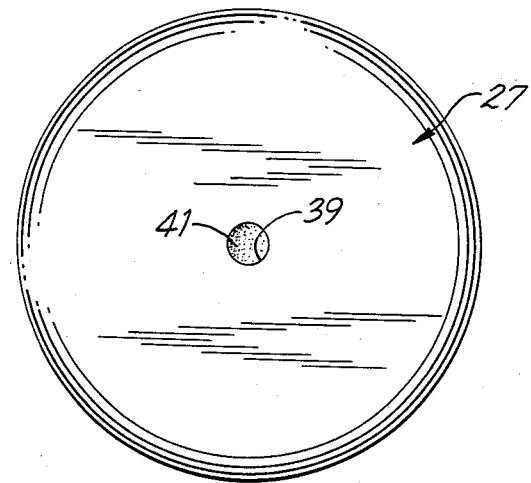
FIG. 2 is a top view of the container.
Figure 4:
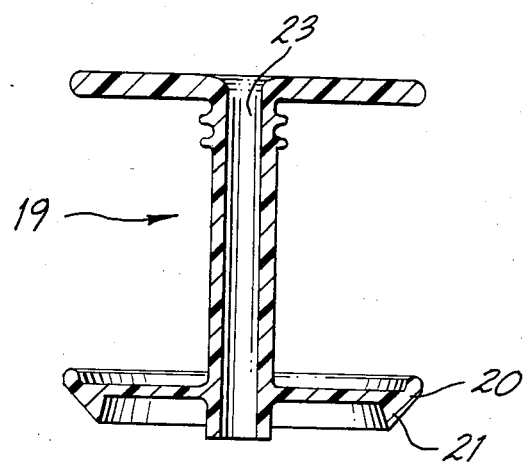
FIG. 4 is cross section of the frame of the culture bottle assembly of the invention.

Referring now to the drawings:

A container 11 is divided into a first lower compartment 13 and a second upper compartment 15 by means of an internal flange 17. A frame 19, as shown in FIGS. 2 and 4 is provided for insertion into the second upper compartment 15. The frame 19 has a lower peripheral edge 20 which generally conforms to the shape of internal flange 17. A resilient material 21 is disposed on the lower peripheral edge 20. The lower peripheral edge 20 and resilient material 21 are sized and dimensioned to engage flange 17 and form a fluid tight seal. A fluid conduit 23 is provided through the frame 19 for insertion of a fluid specimen into the first lower compartment 13. A fluid medium 25 is disposed in the first lower compartment 13 for incubating the fluid specimen when desired. During the process of filling with media the normal oxygen containing atmosphere might be exchanged by oxygen-free gas, such as nitrogen and $CO_2$. By this an enhanced environment is created to provide growth for anaerobic (oxygen-intolerant) bacteria in the broth and subsequently on the surface of the solid media.

Closure means 27 are provided for closing the second upper compartment 15 and for causing the frame 19 to be moved axially so as to cause engagement of the resilient material 21 with internal flange 17 and to seal the first lower compartment with the second upper compartment.

Figure 3:
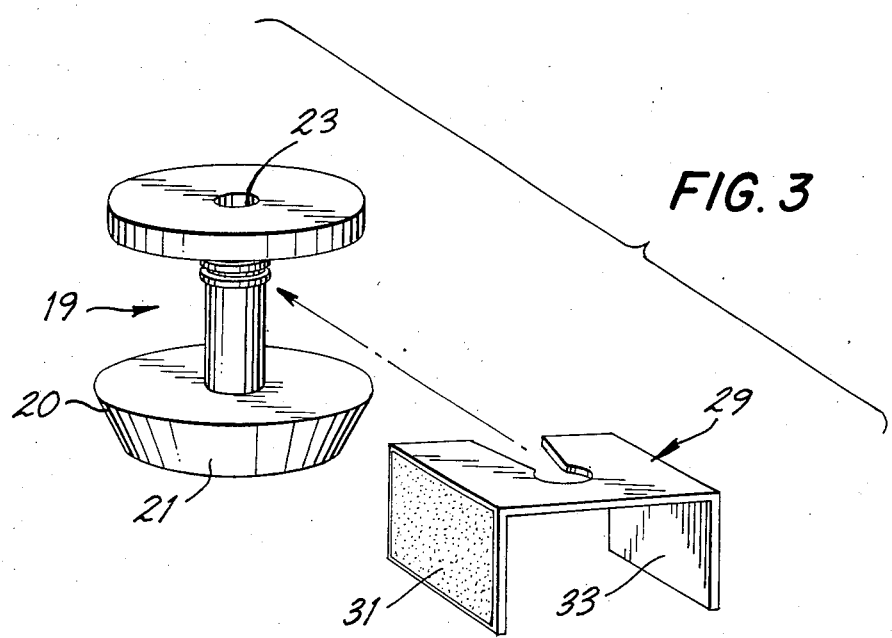
FIG. 3 is a perspective view of the frame of FIG. 2 and a solid media holder showing details of the frame and the solid media assembly.

As shown in FIG. 3, a solid medium holder 29 is disposed around the frame 19 prior to placing the frame into the second upper compartment 15. The solid medium holder contains a suitable solid medium, such as an agar medium. As shown in FIG. 3, the solid medium holder contains two trays 31 and 33. The solid medium holder 29 is made ready for use by first dispensing an agar nutrient material in liquid form at an elevated temperature into the tray sections of the holder 29. The agar nutrient material may be the same or different in each tray. The agar is allowed to cool and solidify before the solid media holder is inserted into mating relationship with the frame 19. While not shown, it should be understood that a third tray could be disposed on the outwardly facing side of solid medium holder 29.

After the solid media holder 29 is moved into mating relationship with the frame 19, the frame 19 is placed into the second upper compartment 15. The frame rests lightly on internal flange 17. Closure means 27, such as a cap, is placed on the open mouth of the container. As shown in FIG. 1, the cap is provided with screw threads as a means for moving the cap into and away from a position where the resilient material 21 mates with the internal flange 17. The displacement means consist of screw threads 35 located in the outside sidewall of container 11 and mating screw threads 37 located in the inside wall of the cap 27.

When the cap is secured firmly into place, the resilient material 21 is compressed against internal flange 17 and a liquid tight seal is formed between the first lower compartment 13 and the second upper compartment 15.

It should be understood that the term "resilient material" as used herein refers to any material which may be sufficiently compressed by the closure means to form a liquid tight seal against internal flange 17 between the first lower compartment and the second upper compartment. Suitable resilient materials include, but are not limited to, polyethylene, polypropolyene, polyurethane, silicone rubber and nylon.

An inoculation port 39 is provided in the cap 27 for injecting a sample into the fluid conduit 23. The inoculation port 29 comprises an opening in the closure means 27 over which a septum 41 is secured. The septum 41 is a suitable material which is capable of being pierced by a cannula or other injection means and which subsequently recloses upon extraction of the cannula. Means, not shown, can be provided for permitting air to penetrate through the fluid conduit 23 and into the first lower compartment 13 for aerobic incubation of the inserted sample. Such means would consist merely of a device with a hollow annular opening therethrough for penetration of the septum 41 to permit air to be admitted into the first lower compartment 13.

The container 11, frame 19, solid medium holder 29 and cap 27 are formed from any suitable material, such as glass, plastic or metal. The container 11 is preferably formed from a transparent material, such as glass or plastic, so that microbial growth on the the solid media can be seen from the outside. The container may be any suitable cross sectional shape but is preferably cylindrical or a regular polygon in shape for ease of manufacture.

During transport and inoculation the cap 27 is in a position such that the resilient material 21 is compressed in mating relationship with the internal flange 17 and the fluid medium is contained in the first lower compartment. A sample is inserted through the septum 41 and downwardly through the fluid conduit 23 into the liquid medium contained in the first lower compartment. After a suitable incubation period, the cap 27 is moved upwardly so that a space is provided between the resilient material 21 and the internal flange 17. The container is inverted to permit the liquid medium to flow from the first compartment into the second compartment. Subsequent growth then occurs on the solid medium contained on the solid medium holder 29.

In accordance with the present invention an extremely simple device is provided for transporting and utilizing a liquid medium followed by subsequent inoculation of a solid medium with a sample incubated in the liquid medium. The culture bottle assembly of the present invention permits transportation of the liquid medium and the solid medium in separate compartments during transportation and provides easy means for transferring the precultured liquid medium into contact with the solid medium when desired.

What is claimed is:
1. A culture bottle assembly comprising:
   1. a container, said container having a first lower compartment for receiving a fluid culture medium and a second upper compartment,
   2. a flange on the interior of the container separating said first compartment from said second compartment,
   3. a frame for holding a solid culture medium tray member adapted for insertion into said second compartment, said frame having a lower edge with a periphery and resilient material around the periphery of the lower edge,
   4. a closure means for said container, and
   5. means for moving said resilient material axially with respect to said container from a sealed position to an open position whereby in the sealed position said resilient material of said frame engages said flange to provide a liquid tight seal between said first compartment and said second compartment and in the open position fluid communication exists between said first and second compartments.

2. A culture bottle assembly in accordance with claim 1 wherein said frame includes a conduit therethrough so that a liquid sample may be inserted through an aperture in said closure means into said first compartment of said container.

3. A culture bottle assembly in accordance with claim 1 which includes a liquid nutrient medium in said first compartment and a tray member having a congealed layer of solid medium in said second compartment.

4. A culture bottle assembly in accordance with claim 1 wherein the container has outer side walls and said means for moving said resilient material comprises screw threads on the outer side wall of said container and mating screw thread on an inner side wall of a cap.

5. A culture bottle assembly in accordance with claim 1 wherein the cross sectional shape of said first compartment is the same as the cross sectional shape of said second compartment.

6. A culture bottle assembly in accordance with claim 1 wherein the cross sectional shape of said first compartment, said second compartment and said internal flange is cylindrical.

7. A culture bottle assembly in accordance with claim 2 wherein said aperture in said closure means has a needle piercable septum placed therein.

8. A culture bottle assembly in accordance with claim 1 wherein the cross sectional shape of said first compartment, said second compartment and said internal flange is a regular polygon.

* * * * *